United States Patent [19]

Matson et al.

[11] Patent Number: 5,210,349

[45] Date of Patent: May 11, 1993

[54] SELECTIVE HYDROGENATION OF CYCLIC POLYENES

[75] Inventors: Michael S. Matson; Harold J. Swindell, both of Bartlesville, Okla.

[73] Assignee: Phillips Petroleum Company, Bartlesville, Okla.

[21] Appl. No.: 845,907

[22] Filed: Mar. 4, 1992

Related U.S. Application Data

[62] Division of Ser. No. 724,069, Jul. 1, 1991, Pat. No. 5,128,296.

[51] Int. Cl.$^5$ ............................................... C07C 2/74
[52] U.S. Cl. ................................. 585/255; 585/250; 585/273; 585/277; 585/325
[58] Field of Search ............... 585/250, 255, 273, 277, 585/325

[56] References Cited

U.S. PATENT DOCUMENTS 3,804,914 4/1974 Fahey .
3,925,494 12/1975 Fahey .
4,204,080 5/1980 Bledso, Jr. et al. ................. 585/947

OTHER PUBLICATIONS

Fahey, "Homogeneous Olefin Hydrogenation Catalyzed by Dichlorodicarbonyl-bis(triphenylphosphine(-ruthenium (II);" *J.Org. Chem.*, vol. 38, No. 19, (1973), pp. 3343-3348.

Fahey, "Selective Hydrogenation of 1,5,9-Cyclododecatriene to Cyclododerene Catalyzed by Ruthenium Complexes", *J. Org. Chem.*, vol. 38, No. 1, (1973), pp. 80-87.

*Primary Examiner*—Patrick P. Garvin
*Assistant Examiner*—E. D. Irzirski
*Attorney, Agent, or Firm*—Ryan N. Cross

[57] ABSTRACT

Cyclic polyenes are selectively hydrogenated to cyclic monoenes under suitable hydrogenation conditions in the presence of an activated ruthenium catalyst complexes. The ruthenium catalyst complex is activated by hydrogenating a minimal amount of cyclic polyene under suitable hydrogenation conditions.

18 Claims, No Drawings

SELECTIVE HYDROGENATION OF CYCLIC POLYENES

This application is a division of application Ser. No. 07/724,069, filed Jul. 1, 1991, now U.S. Pat. No. 4,128,296.

This invention pertains to the selective hydrogenation of cyclic polyenes.

Selective hydrogenation of cyclic polyenes to cyclic monoenes is very difficult to accomplish in high yields. The use of ruthenium for the preparation of cyclic alkenes, the ruthenium being in elemental form, is discussed in U.S. Pat. No. 3,391,206 to Hartog. Such reduction is non-selective with respect to reducing cyclic polyenes to cyclic monoenes as opposed to by-products such as cycloalkanes and cyclic dienes. The use of ruthenium-ligand complexes as catalysts has been discussed as suitable for the selective reduction of cyclic polyenes to cyclic monoenes in U.S. Pat. No. 3,925,494 and U.S. Pat. No. 3,804,914 both to Fahey. Furthermore the use of Lewis bases as selectivity agents to further increase selectivity of hydrogenation is discussed in the article by Fahey in J. Org. Chem. 38, 80–87 (1973). However, even with these selectivity agents at work, it is difficult to achieve the desirable high yields of the desired monoenes with a minimum of by-products created from over hydrogenation and exothermic internal type ring closure reactions to form polycyclics.

It is therefore an object of this invention to increase the yield of cyclic monoenes from the hydrogenation of cyclic polyenes.

It is another object of this invention to decrease the amount of by-products created during hydrogenation of cyclic polyenes to cyclic monoenes.

It is a further object to increase the purity of the cyclic monoene reaction product in a process to hydrogenate cyclic polyenes to cyclic monoenes while maintaining relatively short reaction times with relatively low pressures and temperatures.

It is yet another object of the invention to improve the catalytic activity of a catalyst for use in hydrogenation of cyclic polyenes.

Accordingly, there is provided a process for activating a catalyst comprising contacting the catalyst with hydrogen, a solvent and a cyclic polyene, wherein the solvent is present in an amount greater than about 50 volume percent and the cyclic polyene is present in an amount less than about 50 volume percent based on the total volume, under hydrogenation conditions to produce an activation effluent comprising an activated catalyst, a cyclic monoene product and said solvent.

There is further provided a process for hydrogenating polyenes utilizing a catalyst activated by the above process.

The cyclic polyenes that can be employed in the practice of this invention comprise any polyunsaturated olefin having at least 6 carbon atoms and at least 2 ethylenic double bonds. Suitable cyclic polyenes include cyclododecatriene, 4-n-butylcyclododecairiene, 2,4-dimethylcyclododecatriene, 1-cyclohexylcyclododecatriene, 1-phenylcyclododecatriene, 1,5-cyclooctadiene, 1,4-cyclooctadiene, 1,4-cyclohexadiene, 1,3-cyclohexadiene, bicyclo[2.2.1]hepta2,5-diene, bicyclo[2.2.2]octa-2,5-diene, and the like, and combinations of any two or more thereof. The preferred cyclic polyene is 1,5,9-cyclododecatreine.

Suitable catalyst complexes that can be employed in the practice of this invention include ruthenium catalyst complexes which comprise ligand-complexed divalent ruthenium(II) compounds. The term divalent ruthenium is employed herein to describe a ruthenium atom which has two of its electrons participating in chemical bond formation.

In general, the ruthenium(II) catalyst complexes that can be advantageously employed in the process of this invention can be described by Formula A:

$$L_n RuX_m \qquad (A)$$

wherein L is a ligand selected from $NR_3$, $PR_3$, $AsR_3$, $SbR_3$, $SR_2$, $ROH$, $CO$, $R_3P-R'-PR_2$ and pyridine; each R being the same or different and being selected from alkyl, cycloalkyl and aryl radicals and combinations of any two or more thereof, R' is an alkylene radical; X is a halogen or hydrogen; n is an integer of 2, 3 or 4; m is an integer of 2 or 3; and the sum of n+m is the integer of 4, 5 or 6. Where L is a ligand represented by the general formula $R_2P-R'-PR_2$ such a ligand can function as two of the L ligands of Formula A. Preferably, each R radical contains 1 to 12 carbon atoms. Suitable R radicals include methyl, ethyl, n-butyl, cyclohexyl, n-dodecyl, phenyl (hereinafter sometimes referred to as Ph), benzyl, p-tolyl, 4-n-hexylphenyl, 3,5-dimethylphenyl, 2-naphthyl, and the like. Preferably, each R' radical contains 1 to 4 carbon atoms.

A preferred ruthenium(II) catalyst complex can be described by Formula B:

$$(LL)_p(CO)_q RuX_2 \qquad (B)$$

wherein LL is a ligand selected from $NR_3$, $PR_3$, $AsR_3$, and $SbR_3$, p is an integer of 2 or 3, q is an integer of 1 or 2, the sum of p+q equals the integer 4, and R and X are as previously defined. Even more preferred are ruthenium(II) catalyst of Formula B wherein p and q are each the integer 2.

Illustrative of individual ruthenium(II) catalyst complexes that can be employed in the practice of this invention are those represented by the formulas $(Ph_3P)_2(CO)_2RuCl_2$ $(Ph_3P)_3(CO)RuH_2$, $[(CO)_2RuCl_2]_x$, $(C_5H_5N)_4RuCl_2$, $(C_5H_5N)_2(CO)_2RuCl_2$, $[Ph_2PCH_2CH_2PPh_2]_2RuCl_2$, $(Ph_3P)_3RuCl_2$, $(Ph_3P)_2(CO)_2RuHCl$, $(Ph_3P)_3(CO)RuCl_2$, $(Ph_3P)_3(CO)RuHCl$ and the like and combinations of any two or more thereof. The presently preferred ruthenium(II) catalyst is $(Ph_3P)_2(CO)_2RuCl_2$. In the foregoing, Ph represents phenyl, Et represents ethyl, $C_5H_5N$ represents pyridine, and x is an integer of at least 2 and indicates the polymeric nature of the complex. If desired, complexes such as $(Ph_3P)_3(CO)RuCl_2$ can be transformed to the more preferred polycarbonyl complexes such as $(Ph_3P)_2(CO)_2RuCl_2$ by passing carbon monoxide into a refluxing solution of the monocarbonyl complex in a high boiling polar solvent, e.g., 2-methoxyethanol.

Additional ruthenium catalysts and methods for their preparation are disclosed in U.S. Pat. No. 3,804,914 the disclosure of which is hereby incorporated by reference.

Preferably, the activation of the ruthenium catalyst and the hydrogenation process utilizing the resulting activated catalyst will be performed in the presence of a selectivity agent. Typically such selectivity agents are ligand-forming compounds selected from the group consisting of CO, NR$_3$, PR$_3$, AsR$_3$, R being as previously defined. The presently preferred ligand-forming compound is the PR$_3$ compound triphenylphosphine (PPh$_3$). The ligand-forming compound is present during the hydrogenation process in quantities in excess of the mole ligand requirements of the ruthenium catalyst complex. In general, the ligand mole excess is within the range of from about 0.001 mole to about 50 moles, more preferably within the range of from 5 moles to 25 moles for NR$_3$, PR$_3$ and AsR$_3$ compounds, per mole of catalyst complex. If CO is employed, it is more preferred that the ligand mole excess be in the range of from about 0.001 mole to about 5 moles per mole of catalyst complex. As the amount of solvent employed can vary, it will generally be desirable that the concentration of the excess ligand in the reaction mixture be in the range of from about 0.001 mole to about 1 mole of excess ligand per liter of reaction mixture and preferably in the range of from 0.01 mole to 0.5 mole of excess ligand per liter of reaction mixture, for ligands other than CO. When CO is employed as the excess ligand, its concentration as excess ligand will generally be in the range of from about 0.001 mole to about 0.1 mole of CO per liter of reaction mixture. Higher concentrations of excess CO may tend to deactivate the catalyst.

Although amounts of the ligand-forming compounds are listed above for illustrative purposes, it is preferred that the concentration of ligand-forming compounds be optimized. Generally, an increase in the ligand-forming compound, such as triphenylphosphine, results in increased selectivity and also a decrease in reaction rate. Thus, the concentration of ligand-forming compound should be chosen to optimize selectivity and the reaction rate and will depend on the catalyst and solvent chosen. Generally, for activation or hydrogenation processes, utilizing ruthenium (II) catalyst and either tetrahytrafuran or toluene, the concentration of triphenylphosphine will be in the range from about 0.02M to about 0.05M. As used herein, molar concentration or molarity (M) is expressed as the number of moles solute per liter of solution.

The activation of the ruthenium catalyst is carried out in the presence of a solvent. Optionally, the hydrogenation process using the activated catalyst can be carried out either with or without a solvent.

Suitable substantially non-reactive and/or inert solvents include benzene, toluene, cumene, isooctane, cyclohexane, ethanol, 1-butanol, ethyl acetate, tetrahydrofuran, and the like, and combinations of any two or more thereof. Additional solvents useful in the practice of this invention are ligand forming solvents described by Formulas C and D:

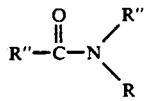

(C)

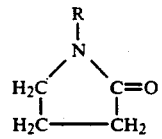

(D)

wherein each R" is the same or different, and each R" is selected from hydrogen, alkyl or cycloalkyl radicals or combinations thereof.

Additionally, combinations of any two or more of the solvents represented by formulas (C) and (D) or chosen from the group including benzene, toluene, cumene, isooctane, cyclohexane, ethanol, 1-butanol, ethyl acetate, tetrahydrofuran, and the like, can be used. Preferably, each R" radical contains from 1 to 12 carbon atoms. Specific examples of preferred solvents are N,N-dimenthylformamide, N,N-dimethylacetamide, N-methylpyrrolidone, N-$\beta$-hydroxyethyl-pyrrolidinone and the like, or combinations of two or more thereof.

The presently preferred solvents for use in the processes of the present invention are toluene and tetrahydrofuran.

The activation process of this invention comprising contacting of cyclic polyene, a ruthenium catalyst complex and a solvent can be carried out under suitable hydrogenation conditions. Typically, such hydrogenation will be carried out in a hydrogen atmosphere. Preferably, a suitable selectivity agent is also present during activation. While the selectivity agent can be any of those listed above, the preferred selectivity agent is triphenylphosphine. The cyclic polyene should be present in a minimal amount; typically less than about 50 volume percent (vol.-%) based on total volume, preferably within the range of from about 5 volume percent to about 45 volume percent, and most preferably from 5 volume percent to 30 volume percent. An excess of solvent is utilized; typically more than about 50 volume percent based on total volume, preferably within the range of from about 55 volume percent to about 95 volume percent, and most preferably from 70 volume percent to 95 volume percent. As used herein, total volume refers to the volume of all the components of the activation or hydrogenation mixture, and typically will include the catalyst complex, the cyclic polyene, the solvent and a selectivity agent. Like the ligand-forming compounds above, the ruthenium catalyst complex will generally be present in a concentration chosen to optimize the reaction. The ruthenium catalyst complex will generally be present in the range of from about 0.001M to about 0.020M and preferably from 0.002M to 0.004M. The temperature and pressure ranges for the activation are generally the same ranges as with the hydrogenation process detailed below. However, for (Ph$_3$P)$_2$(CO)$_2$RuCl$_2$, the preferred range for pressure is from about 10 psig to about 1000 psig, more preferably from 100 psig to 400 psig. The preferred temperature range for (Ph$_3$P)$_2$(CO)$_2$RuCl$_2$ is from about 100° C. to about 200° C., more preferably from 140° C. to 150° C. Generally, complete activation is achieved within a time period of from about 1 to about 6 hours.

After activation the activated ruthenium catalyst complex can be separated from the activation effluent by any suitable conventional separation technique. Typically, the activation effluent is distilled to remove a major portion of solvent, the cyclic monoene product and any by-products and, thus, mostly activated ruthenium catalyst complex is left. Generally, it is not practical or possible to totally separate the activated ruthenium catalyst complex from the other elements of activated effluent. The distilled activated ruthenium catalyst complex can be used in the hydrogenation process.

Generally, it is preferred to add a solvent to the distilled activated ruthenium catalyst complex for hydrogenation runs. Typically, if the activation effluent has been transferred from the hydrogenation reactor to a distillation unit for separation then the solvent will be added to the distilled activated catalyst complex before it is transferred back to the hydrogenation reactor for a hydrogenation process. Any of the above listed solvents can be used for this transfer and the subsequent hydrogenation process; however, tetrahydrofuran is preferred.

The hydrogenation process of this invention comprising contacting suitable portions of cyclic polyene and activated ruthenium catalyst complex can be carried out under any suitable hydrogenation conditions. Typically such hydrogenation will be carried out in a hydrogen atmosphere, and preferably, in the presence of a suitable selectivity agent. While the selectivity agent can be any of those listed above, the preferred selectivity agent is triphenylphosphine. In general, suitable proportions comprise activated cyclic polyene to ruthenium catalyst complex mole ratios of from about 500 to about 50,000, and preferably, from 2,000 to 5,000. A selectivity agent can be present during the hydrogenation process as discussed above. Additionally a solvent can be present during hydrogenation. During the hydrogenation process, typically lower amounts of solvents are preferred for obtaining better selectivity. Thus, solvents, such as tetrahydrofuran, are preferred because of their capacity to better dissolve the ruthenium catalyst complex than solvents such as toluene. Generally, if a solvent is present it will be present in the range of from about 5 volume percent to about 50 volume percent, and preferably, from 5 volume percent to 20 volume percent based on total volume.

After the hydrogenation process, the activated ruthenium catalyst complex can be separated from the activation effluent by any suitable conventional separation technique. Typically, the resulting hydrogenation effluent can be distilled to separate the activated ruthenium catalyst complex from a major portion of the cyclic monoene product, any by-products, and other components of the resulting hydrogenation effluent. As above, it will typically not be practical or possible to totally separate the activated ruthenium catalyst complex from the other components of the activation effluent. The activated catalyst complex can be recycled for utilization in further hydrogenation processes for convenience and economy advantageously if desired since substantially none or very little of the catalyst efficiency is lost during the hydrogenation process even when the process is carried out in the presence of air or oxygen. In general, the recycle of the activated catalyst will be desired because the activated catalyst of the invention not only shows an increase in selectivity over non-activated catalyst on first use but also a continued increase upon subsequent use. Generally, it is preferred to add a solvent to the distilled activated ruthenium catalyst complex for further hydrogenation runs. Typically, if the hydrogenation effluent bas been transferred from the hydrogenation reactor to a distillation unit for separation then the solvent will be added to the distilled activated catalyst complex before it is transferred back to the hydrogenation reactor for a further hydrogenation process. Any of the above listed solvents can be used for this transfer and the subsequent hydrogenation process; however, tetrahydrofuran is preferred.

Suitable hydrogenation temperature conditions vary for both catalyst activation and production of cyclic monomers in accordance with the effective temperature range of the ruthenium catalyst complexes. The ruthenium catalyst complex effective hydrogenation temperature range is defined herein as the difference between the lowest activity temperature of the catalyst and the decomposition temperature of the catalyst complex, e.g., in the case of $(PH_3P)_2(CO)_2RuCl_2$, there is an effective temperature ranges of from about 100° C. to about 200° C. Other catalyst species may have effective temperature ranges within the range of from about 25° C. to about 225° C. Suitable hydrogenation pressures generally are within the range of from about 0 to about 1000 psig. The hydrogenation reaction time required to achieve maximum conversion of a cyclic polyene to cyclic monoene will vary but generally is in the range of from about 0.5 hours to about 16 hours.

EXAMPLES

Example 1

This example illustrates the invention employing an initial activation of catalyst by running an activation batch having greater than 55 weight-% of solvent (of total components) in the reactor.

Into a 300 cc Autoclave Engineers Magna Drive reactor, the following components were charged: 0.36 gram (0.048 millimole) dichlorodicarbonylbis(triphenylphosphine) ruthenium(II); 88.6 grams tetrahydrofuran (THF) (about 56.40 weight-% of total reactants); 66.75 grams cyclododecatriene (CDT); 2.0 grams triphenylphosphine ($PPh_3$). This charge level produced a solution with a Ru concentration of 2.73 millimolar, a 43.6 millimolar concentration of free triphenylphosphine and a CDT concentration of 2.3 molar. The reactor was sealed and purged with nitrogen and then with hydrogen followed by heating to 140° C.

Hydrogen was then introduced into the reactor at 300 psig and the reactor pressure was maintained at 300 psig by addition of hydrogen on demand at a constant pressure through a regulator which was attached to a pressure reservoir of known volume. The amount of hydrogen reacted was determined from the pressure drop in the reservoir. The reaction temperature was maintained at 140° C. for 9.5 hours by internal heat exchanger.

During the reaction, samples were withdrawn through a dip-tube periodically for analysis of CDT and CDE with a gas chromatograph (GC) using 50 meter methylphenyl silicone capillary column. The first final reaction product contained 95.4 weight-% CDE and 0.82 weight-% cyclodecane.

The reactor was cooled and the hydrogen purged from the reactor with nitrogen. The contents of the reactor were transferred to a distillation vessel. The THF was distilled at atmospheric pressure. After removal of the THF, the distillation vessel was evacuated to 1-5 mmHg pressure and the product was distilled overhead until only about 15 cc of material remained in the distillation kettle, this included about 12-13 g CDE that was not distilled off. This slurry product in the kettle was bluish-green and contained the Ru catalyst, free $PPh_3$ and CDE product.

After cooling the kettle to ambient temperature, 26.7 g of THF was added to the kettle. The THF was heated to reflux temperature to insure any residual catalyst or PPh3 on the distillation vessel walls was dissolved. The THF solution could be cooled to 20° C. with complete solubility of the catalyst. The bluish solution was then transferred back to the reactor along with 120 grams of CDT. This results in a 4.2 molar concentration of CDT (Runs 2-10, Table I). The Ru and PPh3 concentrations remained the same, since the total volume was unchanged. The reaction was run at 138° C. at 300 psig. The sample at 3.5 hours reaction time showed 96.28 weight-% CDE and 2.80 weight-% CDA (Run 2i, Table I). The reaction was terminated after 4 hours (by cooling as quickly as possible and removing the hydrogen) to produce 95.5 weight-% CDE and 3.31 weight-% CDA (Run 2ii, Table I). (This demonstrated the need for frequent sampling and the need to terminate the reaction at the correct time to maximize CDE production). The transfer and distillation steps were repeated. Subsequent recycles (Runs 3-10, Table I) were run at lower temperature and/or lower pressures as indicated in Table I.

TABLE I

| Run No. | Reaction time (h) | Reaction temp. (°C.) | Reaction press. (psig) | CDE (Wt %) | CDA (Wt %) |
|---|---|---|---|---|---|
| 1[a] | 9.5 | 140 | 300 | 95.43 | 0.82 |
| 2i | 3.5 | 138 | 300 | 96.28 | 2.80 |
| 2ii | 4.0 | 138 | 300 | 95.90 | 3.31 |
| 3 | 4.5 | 132 | 150 | 97.43 | 1.84 |
| 4[b] | 5.0 | 134 | 150 | 97.55 | 2.29 |
| 5 | 3.8 | 125 | 175 | 96.77 | 1.81 |
| 6 | 2.0 | 140 | 200 | 95.00 | 4.20 |
| 7 | 7.0 | 110 | 160 | 95.50 | 2.97 |
| 8 | 10.0 | 100[c] | 200 | 94.89 | 4.62 |
| 9 | 5.0 | 120 | 150 | 95.06 | 4.21 |
| 10 | 9.0[d] | 115[e] | 220 | 96.19 | 3.47 |

[a]Activation run.
[b]Hydrogen contained 20 ppm carbon monoxide in this and subsequent runs.
[c]Temperature raised to 115° C. for last 2 hours
[d]Increased PPh3 concentration - 55.0 M
[e]Temperature was raised to 135° C. during last hour.

The results in Table I further show that the subsequent recycle runs (Runs No. 3-10), although at considerably lower temperatures and pressures, still produced very satisfactory results of greater than 95% CDE, with the exception of Run No. 8 which was run at very low temperature of 100° C. The results demonstrate that the invention activation process increases reaction rate and decreases reaction temperature and pressure. The highest reaction times for the hydrogenation runs (Runs No. 2-10) were Runs No. 8 and 10. Run No. 8 was run at the low temperature of 100° C. and Run No. 10 was run with an increased PPh3 concentration which is known to increase the reaction time.

COMPARATIVE EXAMPLE I

The run was carried out the same as Example I except that the amount of THF used was only 26.5 grams (16.9 weight % of total reactants in the reactor) and that there was 2.6 g PPh3 in the reaction mixture. The results are shown in Table II.

TABLE II

| Run No. | Reaction time (h) | Reaction temp. (°C.) | Reaction press. (psig) | CDE (Wt-%) | CDA (Wt-%) |
|---|---|---|---|---|---|
| 11[a] | 15.0 | 150 | 400 | 75.0 | 0.8 |

TABLE II-continued

| Run No. | Reaction time (h) | Reaction temp. (°C.) | Reaction press. (psig) | CDE (Wt-%) | CDA (Wt-%) |
|---|---|---|---|---|---|
| 12 | 6.5 | 145 | 200 | 82.92 | 0.81 |

[a]Activation run and the hydrogen contained 20 ppm carbon monoxide.

The results in Table II show that, with low solvent weight percent in the activation run, the selectivity to CDE is very low (75%) even in the presence of a higher phosphine content and under a higher reaction pressure. A higher phosphine content and a reaction pressure are known to increase the selectivity to CDE. Additionally, the presence of carbon monoxide in hydrogenation processes is known not to adversely affect the production of CDE as shown in Runs No. 4-10 of Example I and is reported to aid such production (see U.S. Pat. No. 3,804,914).

The results shown in Tables I and II clearly indicate that the hydrogenation, if the solvent used is greater than 50 weight % of total reactants, (1) can be run at lower temperature and pressure; (2) requires a shorter reaction time; (3) produces a product having higher purity; and (4) produces less by-products.

Example II

This experiment illustrates a scale-up of the invention described in Example I.

The hydrogenation was carried out in a 200 gallon stainless steel Hastelloy C reactor similarly equipped as the 300 cc reactor described in Example I. The reactor was charged with, in the order described, toluene, 1031 lbs. (85.2 weight-%); CDT, 222 lbs; Ru catalyst 1360 grams; and PPh3 9371 grams. The reactor was purged with hydrogen three times, pressured to 400 psig with hydrogen, and then stirred at 375 rpm.

The contents were then heated to 150° C. while hydrogen was continually added to the reactor. The reactor pressure controller was in automatic with a setpoint of 400 psig. This resulted in a continuous flow of hydrogen going through the reactor sparger through the reactor contents and then on to the flare. Attempts to keep the vent valve closed and add only enough hydrogen for reaction resulted in seesaw pressure swings. The reaction ran for 12 hours at which time the crude product contained 92.3 weight-% CDE.

The reactor contents were cooled to 100° C. and 100 gallons were transferred in about 100 gallon units to the 120 gallon steam heated distillation column for distillation. The first 100 gallon unit was distilled and then the second 100 gallon unit was added to the distilled first unit and the combination was distilled. The columns were made of 316 SST and had Koch-Sulzer high efficiency packing. The packing was 6 inches diameter by 13 feet in height.

The toluene was stripped off at 100 mmHg vacuum with the kettle temperature varying from 50° C. to 59° C. About 15 gallons of the CDE was also taken overhead at 10 mm Hg and a kettle temperature of 114° C. Care must be taken to not heat the catalyst/CDE heel above 120° C. when nearing the end of the distillation. Finally a heel of about 15 gallons remains in the kettle. This slurry containing the activated catalyst was yellowish-orange in color.

The catalyst heel was transferred by adding 260 lbs. (68.4 weight-%) of THF to the kettle and refluxing at atmospheric pressure for an hour. To the reactor 956 lbs. of fresh CDT was added and the reactor was purged with hydrogen. The reactor was then pressured to 100 psig with hydrogen. The reactor temperature was about 40° C.

The temperature was then heated to 130° C. over a two-hour period. The reaction started to take up hydrogen at about 125° C. The reactor pressure was increased to 200 psig and held there through the run. The temperature was held at 146° C. The reactor was sampled every hour until the CDE percentage began to decrease. The final anlysis showed 97.1 weight-% CDE and 2.5 weight-% CDA. The total reaction time was about 8½ hours.

The reactor contents were cooled to 100° C. and about the first half transferred to the distillation step and distilled. After the first half was distilled, the remaining reactor contents were added to the first half and the combination distilled.

The THF was stripped off at 160 mmHg to 300 mmHg. The kettle temperature was about 113° C. and an overhead temperature of 18° C. The takeoff to reflux ratio ranged from 30:1 to 1:5. It was possible to remove the THF below levels detected by the GC.

The CDE was stripped off at 2 mmHg. The kettle temperature was 107° C. and the overhead was 20° C.

The total time for the distillation was about 27 hours. The total 96.7% CDE recovered was 789 lbs.

What is claimed is:

1. A hydrogenation process comprising:
   (a) contacting a non-activated ruthenium catalyst with hydrogen, a first cyclic polyene comprising a polyunsaturated olefin having at least 6 carbon atoms and at least 2 ethylenic double bonds, and a first solvent, wherein said first cyclic polyene is present in an amount less than about 50 volume percent and said first solvent is present in an amount greater than 50 volume percent based on the total volume of the components, under hydrogenation conditions to produce an activated ruthenium catalyst and an activation effluent comprising said first solvent and a first cyclic monoene product;
   (b) separating said activated ruthenium catalyst from a major portion of said activation effluent; and
   (c) contacting said activated ruthenium catalyst with a second cyclic polyene comprising a polyunsaturated olefin having at least 6 carbon atoms and at least 2 ethylenic double bonds, and hydrogen
   under suitable hydrogenation conditions to produce a second cyclic monoene product.

2. A process in accordance with claim 1, wherein the contacting of said activated ruthenium catalyst with said second cyclic polyene and said hydrogen is carried out in the presence of a second solvent.

3. A process according to claim 2 wherein said first solvent and said second solvent are selected from the group consisting of benzene; toluene; cumene; isooctane; cyclohexane; ethanol; 1-butanol; ethyl acetate; tetrahydrofuran; compounds of the Formula I:

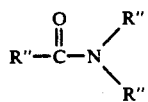

(I)

wherein each R" is individually selected from the group consisting of hydrogen, alkyl and cycloalkyl radicals and combinations thereof; compounds of the Formula II:

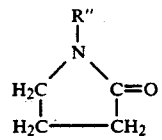

(II)

wherein R" is as previously defined; and mixtures of two or more thereof.

4. A process according to claim 2 wherein said first solvent and said second solvent are selected from the group consisting of toluene and tetrahydrofuran.

5. A process according to claim 1 wherein said first cyclic polyene and said second cyclic polyene is selected from the group consisting of cyclododecatriene, 4-n-butylcyclododecatriene, 2,4-dimethylcyclododecatriene, 1-cyclohexylcyclododecatriene, 1-phenylcyclododecatriene, 1,5-cyclooctadiene, 1,4-cyclooctadiene, 1,4-cyclohexadiene, 1,3-cyclohexadiene, bicyclo[2.2.1]hepta-1,2-diene, bicyclo[2.2.2]octa-2,5-diene, and the like, and combinations of any two or more thereof.

6. A process according to claim 1 wherein said first cyclic polyene and said second cyclic polyene are 1,5,9-cyclododecatriene.

7. A process in accordance with claim 1 further comprising after contacting said second cyclic polyene with said hydrogen and said activated ruthenium catalyst the additional steps of:
   separating said activated ruthenium catalyst from said second cyclic monoene product; and
   recycling said activated ruthenium catalyst for further contacting under hydrogenation conditions.

8. A process in accordance with claim 6 wherein said separating of said activated ruthenium catalyst is by distillation to produce a distilled activated ruthenium catalyst and said recycling comprises adding a third solvent to said distilled activated ruthenium catalyst.

9. A process according to claim 1 wherein said non-activated ruthenium catalyst is selected from the group consisting of ruthenium(II) catalyst complexes and combinations of any two or more thereof.

10. A process according to claim 1 wherein said non-activated ruthenium catalyst is selected from the group consisting of ruthenium(II) catalyst complexes described by formula III and combinations of any two or more thereof:

(III)

wherein L is a ligand selected from $NR_3$, $PR_3$, $AsR_3$, $SbR_3$, $SR_2$, $ROH$, $CO$, $R_3P-R'-PR_2$ and pyridine; each R being the same or different and being selected from alkyl, cycloalkyl and aryl radicals and combinations of any two or more thereof; R' is an alkylene radical; X is a halogen or hydrogen; n is an integer of 2, 3 or 4; m is an integer of 2 or 3; and the sum of n+m is the integer of 4, 5 or 6; and where L is a ligand represented by the general formula $R_2P-R'-PR_2$ such a ligand can function as two of the L ligands of Formula A.

11. A process according to claim 1 wherein said non-activated ruthenium catalyst is selected from the group consisting of ruthenium(II) catalyst complexes described by Formula IV and combinations of any two or more thereof:

$$(LL)_p(CO)_q RuX_2 \quad (IV)$$

wherein LL is a Ligand selected from $NR_3$, $PR_3$, $AsR_3$, and $SbR_3$, each R being the same or different and being selected from alkyl, cycloalkyl and aryl radicals and combinations of any two or more thereof; X is a halogen or hydrogen; p is an integer of 2 or 3, q is an integer of 1 or 2, and the sum of p+q equals the integer 4.

12. A process according to claim 1 wherein said non-activated ruthenium catalyst is selected from the group consisting of those ruthenium(II) catalyst complexes represented by the formulas:

$(Ph_3P)_2(CO)_2RuCl_2$ $(Ph_3P)_3(CO)RuH_2$, $[(CO)_2RuCl_2]_x$, $(C_5H_5N)_4RuCl_2$, $(C_5H_5N)_2(CO)_2RuCl_2$, $[Ph_2PCH_2CH_2PPh_2]_2RuCl_2$, $(Ph_3P)_3RuCl_2$, $(Ph_3P)_2(CO)_2RuHCl$, $(Ph_3P)_3(CO)RuCl_2$, $(Ph_3P)_3(CO)RuHCl$.

13. A process according to claim 1 wherein said non-activated ruthenium catalyst is $(Ph_3P)_2(CO)_2RuCl_2$.

14. A process according to claim 1 wherein said contacting of said non-activated ruthenium catalyst with said hydrogen, said first cyclic polyene, and said first solvent is carried out in the presence of a first selectivity agent which is a ligand-forming compound selected from the group consisting of CO, $NR_3$, $PR_3$, $AsR_3$, R being selected from alkyl, cycloalkyl and aryl radicals.

15. A process according to claim 14 wherein said selectivity agent is triphenylphosphine.

16. A process according to claim 15 wherein said contacting of said second cyclic polyene with said hydrogen and said activated ruthenium catalyst is carried out in the presence of a second selectivity agent which is a ligand-forming compound selected from the group consisting of CO, $NR_3$, $PR_3$, $AsR_3$, R being selected from alkyl, cycloalkyl and aryl radicals.

17. A process according to claim 16 wherein said first selectivity agent and second selectivity agent are triphenylphosphine.

18. A process according to claim 17 wherein:
said first cyclic polyene and said second cyclic polyene are both 1,5,9-cyclododecatriene, and said first cyclic polyene is present in an amount in the range of from 5 volume percent to 45 volume percent based on the total volume;
said first solvent and said second solvent are both tetrahydrofuran and said first solvent is present in an amount in the range of from 55 volume percent to 95 volume percent based on the total volume;
said non-activated ruthenium catalyst is $(Ph_3P)_2(CO)_2RuCl_2$; and
further comprising after said contacting of said second cyclic polyene with said hydrogen and said activated ruthenium catalyst, the additional steps of distilling said activated ruthenium catalyst from said second cyclic monoene product to produce a distilled activated ruthenium catalyst; adding tetrahydrofuran to said distilled activated ruthenium catalyst to form a catalyst solution; and using said catalyst solution in further contacting under hydrogenation conditions.

* * * * *